US011361867B2

(12) United States Patent
List et al.

(10) Patent No.: US 11,361,867 B2
(45) Date of Patent: Jun. 14, 2022

(54) PATHWAYS FOR TREATING PATIENTS

(71) Applicant: H. Lee Moffitt Cancer Center and Research Insitute, Inc., Tampa, FL (US)

(72) Inventors: Alan F. List, Tampa, FL (US); Mark Gerard Schippits, Odessa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 894 days.

(21) Appl. No.: 14/433,364

(22) PCT Filed: Mar. 15, 2013

(86) PCT No.: PCT/US2013/032204
§ 371 (c)(1),
(2) Date: Apr. 2, 2015

(87) PCT Pub. No.: WO2014/055125
PCT Pub. Date: Apr. 10, 2014

(65) Prior Publication Data
US 2015/0324543 A1 Nov. 12, 2015

Related U.S. Application Data

(60) Provisional application No. 61/710,605, filed on Oct. 5, 2012.

(51) Int. Cl.
*G16H 50/50* (2018.01)
*G16H 50/20* (2018.01)
(Continued)

(52) U.S. Cl.
CPC ............ *G16H 50/50* (2018.01); *G16H 50/20* (2018.01); *G16H 20/40* (2018.01); *G16H 40/63* (2018.01); *G16H 70/20* (2018.01)

(58) Field of Classification Search
CPC ........ G06Q 10/00; G06Q 50/00; G16H 10/00; G16H 10/40; G16H 15/00; G16H 20/00;
(Continued)

(56) References Cited

U.S. PATENT DOCUMENTS

2003/0103900 A1* 6/2003 Chachoua .......... G01N 33/5008
424/9.1
2008/0183497 A1* 7/2008 Soon-Shiong ........ G06F 19/322
705/2
(Continued)

FOREIGN PATENT DOCUMENTS

| JP | 2002-109075 | 4/2002 |
|---|---|---|
| JP | 2006-072533 | 3/2006 |
| WO | WO 2011-077353 | 6/2011 |

OTHER PUBLICATIONS

Hsu et al., "Context-Based Electronic Health Record: Toward Patient Specific Healthcare," in IEEE Transactions on Information Technology in Biomedicine, vol. 16, No. 2, pp. 228-234, Mar. 2012, doi: 10.1109/TITB.2012.2186149.*
(Continued)

*Primary Examiner* — Robert W Morgan
*Assistant Examiner* — Charles P Coleman
(74) *Attorney, Agent, or Firm* — Fish & Richardson P.C.

(57) ABSTRACT

Methods, systems, and apparatus, including computer programs encoded on a computer storage medium are provided, including a method for presenting information for treating patients. The method comprises presenting, in a user interface, a pathway for use in treating a patient with a disease and including a combination of therapeutic and diagnostic pathway elements including an integration of diagnostic, radiation, chemotherapy, surgical and other elements. The method further comprises augmenting the pathway including providing controls for accessing additional information associated with a given pathway element, augmenting path-
(Continued)

way elements to include indicators for pricing, efficacy and/or toxicity of a treatment associated with a given treatment element, and augmenting the pathway with a connection to another pathway including providing a link to another pathway at a point in a given pathway that provides information for a related pathway. The method further comprises presenting an augmented pathway to a patient or treating physician.

29 Claims, 9 Drawing Sheets

(51) Int. Cl.
*G16H 20/40* (2018.01)
*G16H 40/63* (2018.01)
*G16H 70/20* (2018.01)

(58) Field of Classification Search
CPC ........ G16H 20/10; G16H 20/13; G16H 20/17; G16H 30/00; G16H 40/00; G16H 50/00; G16H 70/00; G16H 80/00; G16H 50/50; G16H 50/20; G06F 19/325
USPC .......................................... 705/2.3, 2, 3, 20

See application file for complete search history.

(56) References Cited

U.S. PATENT DOCUMENTS

| | | | |
|---|---|---|---|
| 2008/0221923 A1* | 9/2008 | Shogan | G16H 50/20 705/2 |
| 2008/0256490 A1* | 10/2008 | Lord | G06F 19/325 715/835 |
| 2010/0017455 A1 | 7/2010 | Abraham-Fuchs et al. | |
| 2011/0210853 A1* | 9/2011 | Lord | G06F 19/325 340/573.1 |
| 2011/0301977 A1* | 12/2011 | Belcher | G06F 19/345 705/3 |
| 2012/0158391 A1* | 6/2012 | Vaske | G06F 16/2219 703/11 |
| 2012/0231959 A1* | 9/2012 | Elton | G06Q 50/22 506/2 |
| 2013/0006649 A1* | 1/2013 | Rangadass | G06F 19/327 705/2 |
| 2013/0166317 A1* | 6/2013 | Beardall | G06F 19/322 705/2 |
| 2015/0006193 A1* | 1/2015 | Dadlani Mahtani | G16H 10/60 705/2 |

OTHER PUBLICATIONS

Shortliffe et al., "Knowledge engineering for medical decision making: A review of computer-based clinical decision aids," in Proceedings of the IEEE, vol. 67, No. 9, pp. 1207-1224, Sep. 1979, doi: 10.1109/PROC.1979.11436.*

International Search Report and Written Opinion prepared by Sang Won Choi, dated Jul. 7, 2013, 13 pages.

* cited by examiner

PATHWAYS FOR TREATING PATIENTS

CROSS-REFERENCE TO RELATED APPLICATIONS

This application is a National Stage Application under 35 U.S.C. § 371 and claims the benefit of International Application No. PCT/US2013/032204, filed on Mar. 15, 2013, which claims the benefit under 35 U.S.C. § 119(e) of U.S. Provisional Application No. 61/710,605, filed on Oct. 5, 2012. The disclosures of the prior applications are considered part of and are incorporated by reference in the disclosure of this application.

BACKGROUND

This specification relates to collecting and presenting data.

Patients who have a disease, such as cancer, can face a complex course of events associated with treatment. The events can include consultations with doctors and specialists, and laboratory studies that can influence a myriad of choices related to medications, surgery, chemotherapy, radiation and other aspects of treatment. There are many decisions to be made by the patient as well as by the treating professionals. Best practices for treating the course of disease can be embodied in a pathway. The pathway can present a sequence of decisions/steps associated with the treatment of a disease. Pathways have been developed for numerous diseases and represent an author's/institution's progression path for the evaluation/treatment of the disease in patients. In the abstract, these pathways provide clear direction for the treatment of a patient with a given disease. However, the use of pathways often requires additional information in order to identify the best treatment for a given patient or to enable a reasoned recommendation to be made for a next treatment. For example, the cost or toxicity of a treatment and medical insurance are other factors among many which may influence decision making when referencing a pathway.

SUMMARY

This specification describes technologies relating to methods and systems for presenting information used in treating patients.

In general, one innovative aspect of the subject matter described in this specification can be embodied in methods, including a method that comprises presenting, in a user interface, a pathway for use in treating a patient with a disease and including a combination of therapeutic and diagnostic pathway elements including an integration of diagnostic, radiation, chemotherapy, surgical and other elements (e.g., related to other procedures and pharmacotherapy). The method further comprises augmenting the pathway including providing one or more controls for accessing additional information associated with a given pathway element. The method further comprises augmenting pathway elements to include indicators for pricing, efficacy and toxicity of a treatment associated with a given treatment element in the pathway. The method further comprises augmenting the pathway with a connection to another pathway, including providing a link to another pathway at a point in a given pathway to enable quick reference to another pathway from a relevant point of the given pathway. The method further comprises presenting an augmented pathway in a user interface to a patient or treating physician. Other embodiments of this aspect include corresponding systems, apparatus, and computer programs, configured to perform the actions of the methods, encoded on computer storage devices.

These and other implementations can each optionally include one or more of the following features. The pathway can be specific to a form of cancer. Providing one or more controls can further include identifying one or more references germane to or for inclusion in a pathway, identifying updates or comments to the references, and providing one or both when the control is activated. The indicators for pricing can include an estimate of one or more of a wholesale price, co-payments, actual cost, profit or other raw or evaluated financial indicators of a treatment associated with a pathway element, and the method can further include determining one or more of an estimate for a wholesale price, co-payments, an actual cost, profit or other raw or evaluated financial indicators for the treatment. The indicators for toxicity and/or efficacy can include a toxicity and/or efficacy score, and the method can further include calculating a toxicity and/or efficacy score based at least in part on historical information associated with treatment of patients using the pathway. Indicators can also include indicators of effectiveness of treatment, and other indicators such as indicators of appropriateness of positron emission tomography-computed tomography (PET-CT) for surveillance, and time to adjuvant therapy after surgery, among others.

The pathway can include plural integrated pathways. The method can further comprise color-coding the elements based on a type of element such that different therapeutic or diagnostic element types are color-coded to reflect the type of element. The color-coding can include color-coding individual pathway elements and color-coding blocks of elements to define particular portions of the pathway. The additional information can include information to assist in making a decision in association with a decision element in the pathway, clarification information for an element, patient education information, or decision rationale information. The method can further comprise augmenting one or more pathway elements with referral information when the pathway element involves a treatment that is beyond a scope of a current treatment facility. Augmenting the one or more pathway elements with referral information can further include augmenting a pathway element with a control for directly referring a patient to another treating facility or care provider. The method can further comprise linking the pathway to an electronic medical record for the patient.

In general, another innovative aspect of the subject matter described in this specification can be implemented in methods that include a method for presenting treatment information to a patient or treatment professional. The method comprises identifying a disease associated with a patient. The method further comprises identifying a pathway associated with the disease, the pathway including a combination of therapeutic and diagnostic pathway elements including an integration of diagnostic, radiation, chemotherapy and/or graphical and/or surgical elements. The method further comprises using a question and answer paradigm to navigate the pathway to identify a current location on the pathway that is relevant to the patient. The method further comprises presenting an instantiation of the pathway in a user interface including highlighted portions that reflect a path associated with a treatment and evaluation of the patient or providing similar drill-down capabilities with a question and answer tool.

These and other implementations can each optionally include one or more of the following features. Presenting the instantiation of the pathway can further include presenting a forward-looking version of the pathway from a current treatment point for the particular patient and presenting a breadcrumb trail or clinical summary in an outline format and/or graphical format for decisions and selections made previously that resulted in a traversal of the path to the current point. The forward looking version of the pathway can be presented in one frame of a user interface and the clinical summary or breadcrumb trail can be presented in a second different frame of the user interface. The method can further comprise receiving a selection of an element in the forward looking version of the pathway, and the method can further comprise presenting an instantiation of the pathway from a point in the pathway associated with the selection including a highlighted portion reflecting the path traversed in treating the patient. The selection or last stopping point in a traversal can be saved to enable picking up appropriately (e.g., resuming at a specific point) at the next patient visit. The pathway can be an augmented pathway that includes one or more controls for accessing additional information associated with a given pathway element to assist in either evaluating a pathway element or making a decision in association with a decision element in the pathway and one or more indicators for pricing, efficacy and/or toxicity or outcome of a treatment associated with a given treatment element in the pathway. The pathway can provide a clinical summary of past treatment of and potential future treatment options for the patient. The method can further comprise providing a control for expanding or contracting the clinical summary including a control for enabling display of the pathway from a current time point forward, the current time point backward, the entire pathway, or some other time frame. The some other time frame can include providing an expanded portion of the pathway for a first portion of the time frame along with a contracted portion of the pathway for a second portion of the time frame. The expanded pathway may be transmitted (e.g., emailed) to referring physicians to enhance communication. The pathway can also be used in a question and answer interface, e.g., to obtain patient and/or physician answers to questions related to the treatment of the patient. Using the question and answer paradigm to navigate the pathway to identify the current location on the pathway that is relevant to the patient can further comprise linking the pathway to an electronic medical record for the patient to facilitate navigation of the pathway (either current navigation or to enable pick up at a specific progression point for resumption of a consultation at a next visit by the patient). The facilitating can further include providing answers to one or more questions based on information stored in the electronic medical record during navigation. The additional information can include periodicals, drill-down information, teaching tools, resources or presentations. The method can further include receiving data input associated with the pathway, the data input including data received automatically from data capture tools integrated into an electronic medical record and data received from manual inputs of medical staff or a patient (or data previously captured in the EMR), and providing at least one clinical summary that is color-coded and expandable based at least in part on responsibilities or needs of a viewing party.

Particular embodiments of the subject matter described in this specification can be implemented so as to realize none, one or more of the following advantages. For example, a pathway can provide a visual representation of treatment options available to a patient. The pathway can also graphically display the relationships among the elements of the pathway and provide, upon selection of a control, additional information associated with any element, e.g., in the question and answer interface. A pathway can be presented for a given patient that represents a forward or backward looking (or both) perspective of the patient's treatment (e.g., both past and prospective). A clinical summary can be presented of a path traversed for a given patient to a treating professional along with a prospective portion of the pathway that represents both a current decision point and future treatment decisions for treatment of a given disease. Augmentation of the pathway can enable ready access to supporting information and may support direct referrals to other experts in another institution. The integration of therapeutic, surgical, pharmacological and other disciplines ensures that a whole patient approach can be taken when treating the patient using a pathway. The pathways approach can enhance interdisciplinary collaboration/effectiveness of nursing, physician and case management pathways and tools and can be integrated to create an integrated program for health care transformation. Patient care can be integrated with materials that enhance patient education for knowledgeable participation and decision-making Pathways and other references can be used with payers to streamline pre-authorization and used to review staffing/experience for payers and providers, and provide measures of quality and safety indicators. Pathways can empower patients with supporting materials, which can enable patients to participate more fully in the health care decisions and cost containment (e.g., patients as gatekeepers). Pathways can provide discrete decision actions as measurables of quality and safety of management selections. Pathways can enhance the patient experience and can be a differentiator when comparing care provided by one treatment center over another. Surveys of patients may reflect increased customer satisfaction when tools such as pathways are made available to the patients. The use of pathways facilitates more information flow to the patient in an easy and readily understandable fashion, thus further involving the patient in the success of the treatment programs. Engaged patients tend to be happier with their overall care, and as such, the use of pathways may facilitate not only a better patient experience but also a better rating of a given care provider or institution. Ratings may be used not only to compare institutions but also when evaluating a service provider, such as for selection, for inclusion in a program, for compensation, or for other benefits or in other decision making processes.

The details of one or more embodiments of the subject matter described in this specification are set forth in the accompanying drawings and the description below. Other features, aspects, and advantages of the subject matter will become apparent from the description, the drawings, and the claims.

DETAILED DESCRIPTION

This disclosure describes systems and methods for presenting a pathway for treatment of a disease (e.g., specific to a form of cancer). The pathway can be presented, for example, in a user interface, and can include interconnected elements that represent various possible treatments and decisions to be made by the patient, e.g., in consultation with treating professionals (e.g., physicians, researchers, specialists or other caregivers). Relationships among elements in the pathway can be indicated using direction arrows that connect related elements. The pathway can represent a superset of past decisions, and prospective paths forward that includes the treatment path ultimately taken by the patient. The pathway can be used, for example, by the physician to explain various treatment options. The graphical nature of a pathway can make it easier for the patient to understand various treatment options and to plan accordingly. The pathway can also be used by the treating professional, for example, during a planning stage for laying out possible treatments for patients having a disease. Each pathway can also be augmented so that patient-specific information is presented, and information (e.g., periodicals, online articles, etc.) associated with any element in the pathway can also be made available for access by the patient and/or physician.

Figure 1:
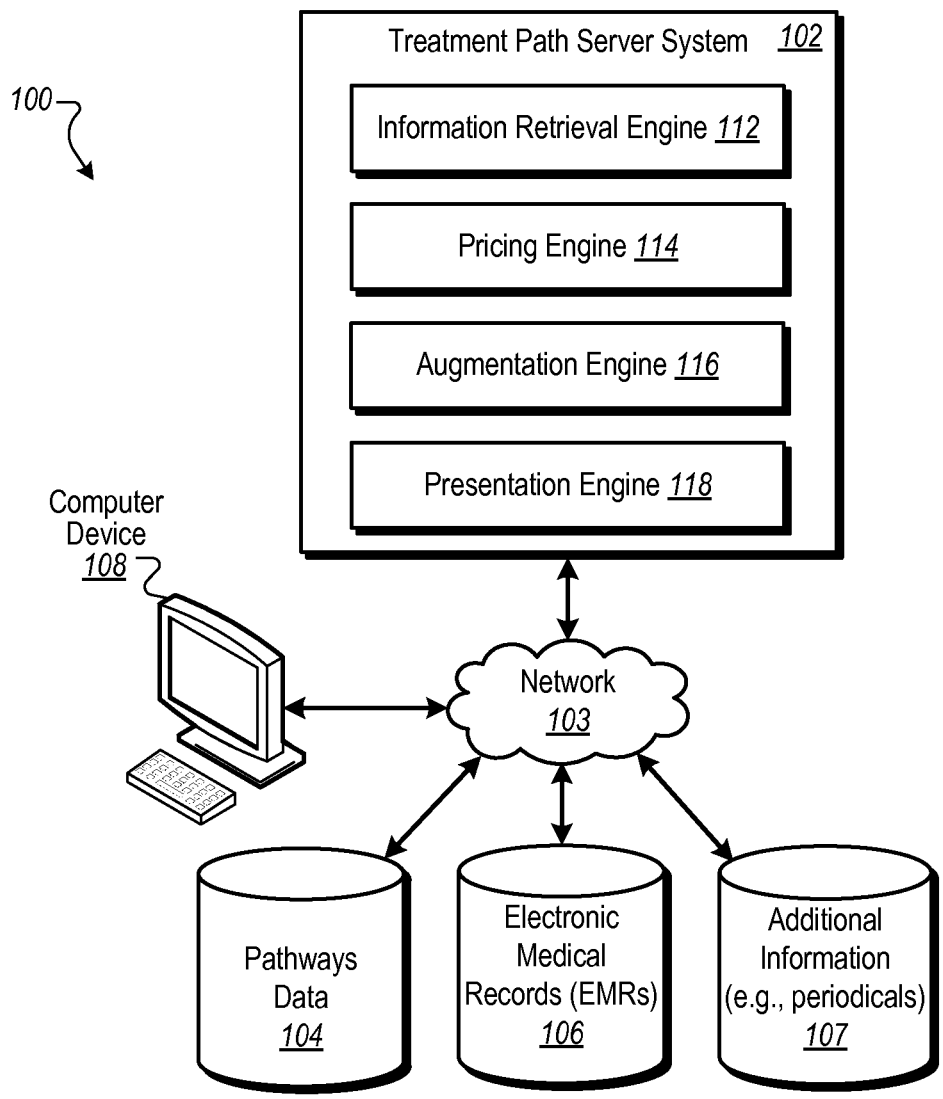
FIG. 1 is a block diagram of a system for using pathways to present treatment information associated with patients.

FIG. 1 is a block diagram of a system 100 that uses pathways to present treatment information associated with patients. The system 100 can be used, for example, to present a pathway in a user interface, where the pathway is used in treating a patient with a disease (e.g., cancer). The pathway can include a combination of therapeutic and diagnostic pathway elements including an integration of diagnostic, radiation, chemotherapy, surgical and other elements. For example, the pathway can be presented to a user (e.g., doctor, patient, etc.) as a network of interconnected elements that show various treatment paths for a patient having a disease (e.g., cancer), e.g., to be used as a tool by the physician to explain possible treatment options. In some implementations, a pathway that is presented can represent plural integrated pathways, e.g., separate pathways related to the same kind of cancer but that may involve different courses of treatment.

As shown in FIG. 1, the system 100 includes a treatment plan server system 102 that performs the bulk of the processing regarding pathways. The treatment plan server system 102 is connected (e.g., over a network 103) with pathways data 104, electronic medical records (EMRs) 106, and additional information 107. Information related to pathways can be presented on one or more computer devices 108 (e.g., used by patients, doctors and other medical staff), also connected to the network 103. The computer devices 108 can include personal computers, laptop computers, mobile devices, or any other computing devices suitable for providing and/or using information in the system 100. For example, non-mobile devices may be in the same hospital, or located in different places, and connected by the network 103, e.g., using a combination of the Internet, local area networks (LANs), wide area networks (WANs), and other networks. Processing that occurs within the system 100 can adhere to patient security and privacy laws and guidelines, including Health Insurance Portability and Accountability Act (HIPAA) and other rules and regulations. Other components of the system 100 can also exist.

The pathways data 104 can include the basic pathway data that defines the elements and connectivity thereof for a given pathway for the treatment of a disease. For example, the pathways data 104 can include one or more treatment pathways for pancreatic cancer, different treatment pathways for prostate cancer, different treatment pathways for lung cancer, and so on.

The electronic medical records (EMRs) 106 can include medical records that are stored for patients at one or more hospitals and/or other treatment facilities. EMRs 106 that are accessed and used by the system 100 can include insurance information for patients maintained by insurance providers, patient information maintained by government agencies, and so on. In some implementations, the EMRs for a patient can be linked directly to one or more pathways associated with the patient.

The additional information 107 can include periodicals, drill-down information, teaching tools, resources, presentations, articles, studies, on-line information, referral information, multi-media items and the like. As an example of how the additional information 107 may be used, a pathway that is presented to a user (e.g., a patient or doctor) can include one or more controls (shown in the later figures as icons) that can serve as links to underlying information. Selecting the control (e.g., icon), for example, can result in displaying a corresponding article or online resource that is pertinent to an element in the pathway. For example, an article on the side effects of a particular form of chemotherapy can be accessible from an icon/link that appears next to a chemotherapy element in a pathway. While the additional information 107 may include mostly written information associated with a topic, the additional information can also include images, videos, audio, spreadsheets, tables, graphs, notes from treating physicians and so on.

The treatment plan server system 102 can include plural engines. An information retrieval engine 112 can access information from pathways data 104, EMRs 106 and additional information 107 in order to carry on the functions of the system 100. For example, when a request is received from the computer device 108 to display a particular pathway, the information retrieval engine 112 can look up information for the pathway in the pathways data 104, e.g., using a pathway identifier and/or other techniques. If patient-specific information is needed to display the requested pathway, e.g., to create an instantiation of the pathway that shows the patient's current treatment progression along with augmented data related to future treatment steps, then the information retrieval engine 112 can access information for the patient in the EMRs 106 and combine that with information in the pathways data 104. If a user makes a selection corresponding to wanting to review a particular periodical associated with an element in the pathway, then the information retrieval engine 112 can access the additional information 107, e.g., using an identifier for the periodical or a universal resource locator (URL) for the periodical.

A pricing engine 114, for example, can look up and/or estimate wholesale prices, co-payments, actual costs, profit or other raw or evaluated financial indicators associated with various treatments associated with a pathway element for a given institution. For example, for an element in the pathway that represents surgery for the patient's cancer, there may be many costs that the pricing engine 114 can determine, e.g., by looking up the prices charged by the hospital and applying adjustments to the prices based on the patient's insurance plan(s) and/or whether a clinical trial or study is paying part or all of the cost. The pricing information can include wholesale and/or actual costs as well as what the patient's expected out-of-pocket co-pays, lifetime maximums, and claims incurred to date. All of this information can be made available within a presented pathway, e.g., in the form of indicators that are used to augment the pathway.

An augmentation engine 116 can augment a pathway in one or more ways. For example, augmentation can include providing one or more controls for accessing additional information (e.g., links to related articles) associated with a given pathway element. In another example, augmentation can include augmenting pathway elements to include indicators for pricing (e.g., determined by the pricing engine 114), efficacy and/or toxicity of a treatment associated with a given treatment element in the pathway. For example, for a pathway element related to a course of chemotherapy treatment, the augmentation engine 116 can augment a pathway with one or more user-selectable indicators that can display information related to liver toxicity, hair loss, fatigue, nausea, and any other side effects of a particular chemotherapy treatment. In some implementations, the information presented can be tailored to the particular patient's expected dosages of medications, specific cancer drugs, and/or other factors unique to the patient. The augmentation engine 116 can also augment a pathway to present an instantiation of the pathway that is unique to a particular patient. For example, the augmentation engine 116 can identify the patient's specific path through the pathway, e.g., an up-to-date view, and can also outline parts of the pathway that are likely or possible based on the patient's current point in the pathway. The up to date view can be of the form of a clinical summary of treatment and/or a visual representation of traversal along the pathway based on prior treatment decisions. In some implementations, icons that are used to augment pathways, including icons related to toxicity, cost, efficacy or other subjects, may be used (e.g., by the physician) to make related entries into EMR systems.

In some implementations, the augmentation engine 116 can augment a pathway with other data. For example, various clinical quality indicators, benchmarks, and educational case vignettes may also be integrated into the clinical pathways and related products/offerings. Clinical quality indicators may include specific measures of timeliness, adherence, associated outcomes, and/or other data capture components as well as the ability to post related summaries, statistics, indications for data collection, or highlighting importance of these indicators on the pathways themselves. Similarly, the pathways may incorporate existing external benchmarks or specifically crafted indicators to drive key areas for practice alignment or outcomes. Finally, case vignettes that support the specifics of clinical pathways may be integrated into teaching tools, either accessible online from the pathways themselves or available as adjunctive educational programs.

In some implementations, the augmentation engine 116 can generate a bread crumb trail or clinical summary in an outline format and/or graphical format familiar to physicians, e.g., for the patient that includes decisions and selections made previously that resulted in the traversal of the path to the current point. For example, the bread crumb trail can include a numbered list of events, decisions, etc. that correspond to an instantiation of the pathway that is highlighted to indicate the patient's path and current position, and for use in an EMR patient portal or for communication to referring physicians.

A presentation engine 118 can provide instructions for presenting the augmented pathway within a graphical user interface of the computer device 108 used by the patient or treating physician. For example, the presentation engine 118 can handle preparing the data to be displayed and can also receive requests from the computer device 108, e.g., to provide additional information, such as if the user has selected a control to access an article on the side effects of a particular chemotherapy treatment. In some implementations, the presentation engine 118 can also support functionality by which a physician or other professional can design a pathway, print a pathway, and/or information about the pathway.

Figure 2:
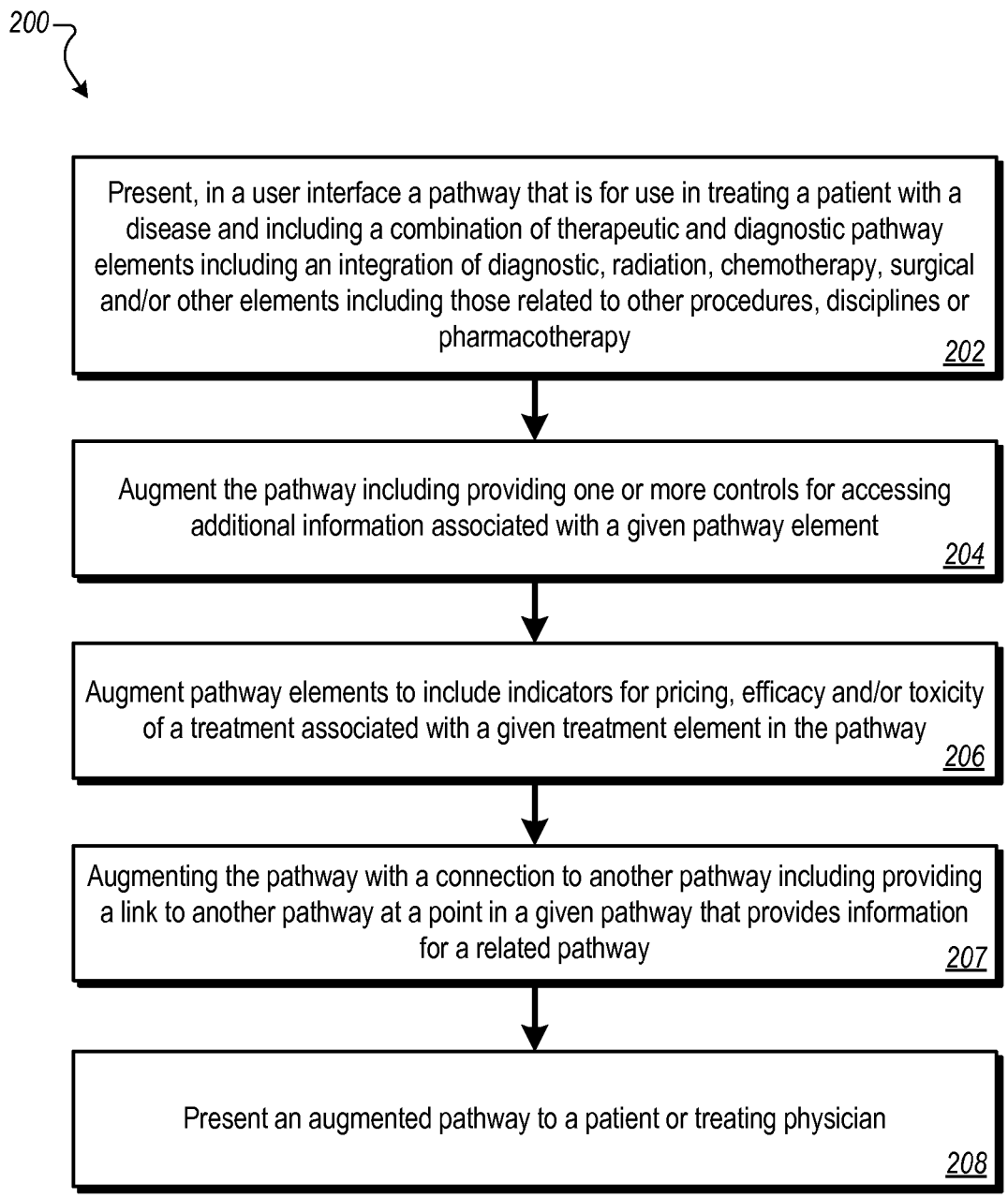
FIG. 2 is a flow diagram of an example process for presenting an augmented pathway for use in treating a patient with a disease.

FIG. 2 is a flow diagram of an example process 200 for presenting an augmented pathway for use in treating a patient with a disease. In some implementations, components of the treatment path server system 110 can perform steps of the process 200 using instructions that are executed by one or more processors. FIG. 1 is used to provide example structures for performing the steps of the process 200.

A pathway is presented in a user interface, the pathway for use in treating a patient with a disease and including a combination of therapeutic and diagnostic pathway elements, including an integration of diagnostic, radiation, chemotherapy and/or surgical elements (202). As an example, the presentation engine 118 can generate pathway information using information obtained from the pathways data 104 and other sources, and provide the pathway information to the computer device 108 for display to a patient or physician.

Figure 3A:
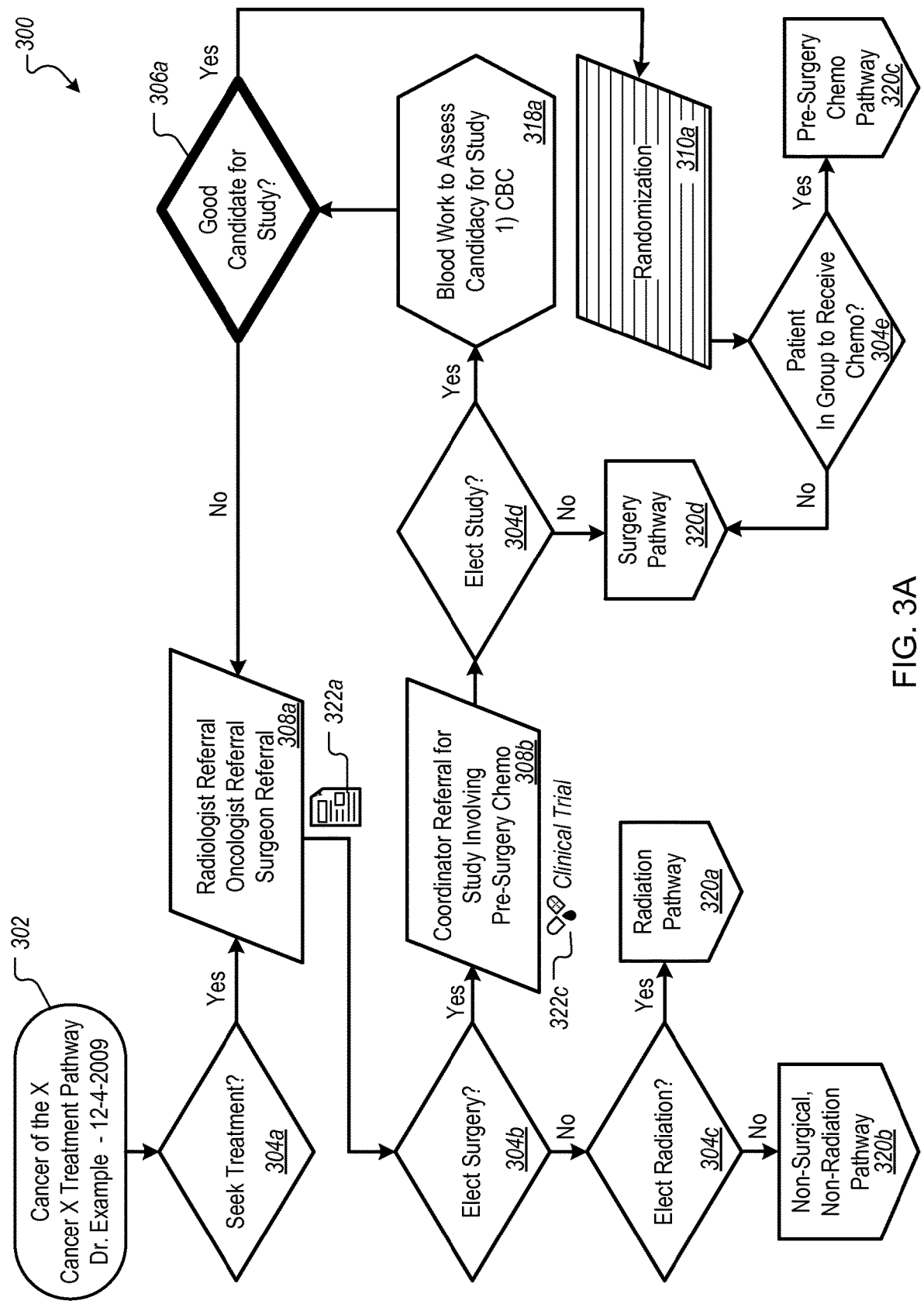
FIGS. 3A-3B collectively show an example pathway for a specific type of disease.
Figure 3B:
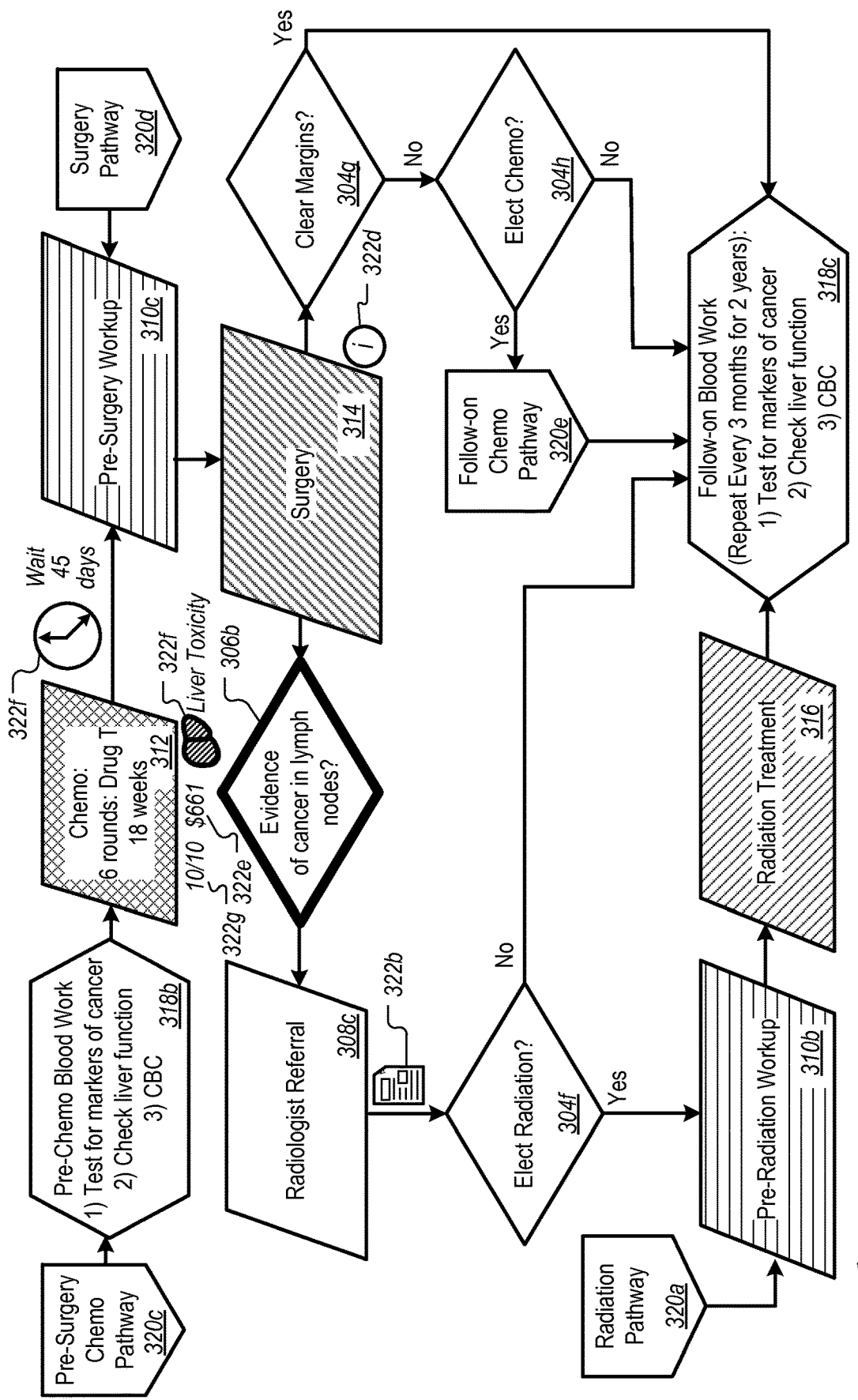

For example, FIGS. 3A-3B collectively show an example pathway 300 for a specific type of cancer, as identified by a beginning-of-pathway marker 302 that includes at least a pathway name, an author and a date. As shown in this example, the pathway 300 includes single-factor decision boxes 304*a*-304*h* (e.g., for objective, discrete decisions) and complicated decision boxes 306*a*-306*b* (e.g., with bolded outlines for decisions requiring multiple factors and additional clinical knowledge or judgment). The decision boxes 304*a*-304*h* and 306*a*-306*b* can have associated yes and no branches that feed into other elements of the pathway 300.

In some implementations, parallelogram shapes having different shading can be used for elements in the pathway 300 that are diagnostic and therapeutic processes of patient care. For example, processes 308*a*-308*c*, shown as unshaded parallelograms, can represent referrals associated with various types of physicians and specialists. Processes 310*a*-310*c*, e.g., shown with using horizontal shading, can represent work-ups (e.g., pre-surgery, pre-radiation, etc.). In some implementations, processes representing work-ups can be indicated using blue outlines. Different types of elements in pathways can be represented in different ways, such as using different fonts and/or styles, color-coding, shading and/or other techniques, so that related elements can be easily distinguished from other elements in the pathway and/or such that different therapeutic or diagnostic element types are color-coded to reflect the type of element. In some implementations, color-coding of elements in a pathway can be based on a type of element such that different therapeutic or diagnostic element types are color-coded to reflect the type of element.

For example, process element 312, shown with crosshatch shading, can represent a form of chemotherapy treatment, which may also be represented with a specific color. Surgical treatment element 314, e.g., shown with back-slash shading, can represent a surgical treatment element of the pathway 300, which may also be represented with a specific color. Process element 316, e.g., shown with forward-slash shading, can represent a radiation treatment element, which may also be represented with a specific color (e.g., red). In some implementations, hexagonal boxes can be used to list events and/or frequencies that are to be repeated until progression/recurrence, e.g., blood work elements 318a-318c.

Pathway markers 320a-320e, for example, can be used to indicate off-page connectors to another pathway, such as Pre-Surgery Chemo Pathway marker 320c that appears on FIG. 3A, indicating a connection to the same Pre-Surgery Chemo Pathway marker 320c that appears on FIG. 3B. Some pathway markers can also be used to label an entry point into a pathway.

The pathway is augmented, including providing one or more controls for accessing additional information or links associated with a given pathway element (204). For example, the augmentation engine 116 can generate one or more controls 322a-322d for accessing additional information associated with a given pathway element. The additional information can be used, for example, to assist in either evaluating a pathway element or making a decision in association with a decision element in the pathway. Example information accessible from the controls can be related to informational lines, periodicals, guidelines, references, sets of drug-specific information, clinical trials, time periods off treatment or to wait for treatment, referral opportunities, referral team details, referral team statistics, radiation therapy information, rash, nausea, diarrhea, and other treatment or associated information and/or side effects. In some implementations, the treatment path server system 110 can identify one or more periodicals for inclusion in a pathway, identifying updates or comments to the periodicals, and providing one or both when the control is activated. In some implementations, controls can be provided for directly referring a patient to another treating facility or care provide (e.g., where the treatment called for requires more specialization or different facilities than that available by the referring physician). For example, the referral information can be added when the pathway element involves a treatment that is beyond the scope of a current treatment facility. In some implementations, drug-related controls can be provided for connecting the physician directly to tools for ordering medications for patients and/or checking on the current and/or past medications taken by the patient.

Pathway elements are augmented to include indicators for pricing, efficacy and/or toxicity of a treatment associated with a given element in the pathway (206). As an example, the augmentation engine 116 can generate one or more controls 322e-322g for pricing (e.g., first data bank average wholesale prices (AWP) for regimen and supportive care), efficacy (e.g., chemo intensity ratings of efficacy/toxicity on a scale of 1-10), and toxicity, respectively. Toxicity information can include organs/systems affected such as the indicators shown for liver, cardiac and neural toxicities.

The pathway can also be augmented with a connection to another pathway, including providing a link to another pathway at a point in a given pathway to enable quick reference to the another pathway from a relevant point of the given pathway (207). For example, the connections in the pathway 300 can include other indicators (e.g., for nursing, patients, discharge, post-operative care, complications, prevention, and/or others), each of which can be used to access and/or navigate to corresponding pathways.

An augmented pathway is presented in a user interface to a patient or treating physician (208). For example, the pathway 300 shown in FIGS. 3A-3B can be presented on the computer device 108. Standard and/or state-of-the-art Visio capabilities can be used to present the information. For example, in situations in which too much information exists as will fit on a screen, the information can be split onto multiple pages or portions of the same pathway, and pathway markers 320a-320e can be used to indicate off-page connectors to another pathway or the same pathway. In some implementations, additional controls can be presented for navigating to other parts of a pathway, to zoom in or out of a display, or to pan the display in different directions.

In some implementations, the user can select an element in a forward looking version breadcrumb trail and the process 200 can further comprise presenting an instantiation of the pathway from a point in the pathway associated with the selection including a highlighted portion reflecting the path traversed in treating the patient. The selection can be stored to enable picking up appropriately at the next patient visit. For example, by selecting any one individual element (e.g., surgical treatment element 314) in the pathway 300, the elements leading up to that element and corresponding to the patient's treatment can be highlighted. In some implementations, the pathway can further provide a clinical summary of past treatments of and potential future treatment options for the patient. In some implementations, outcomes and other factors can be displayed that are based on information from referral literature or internally generated for decision support.

Figure 3C:
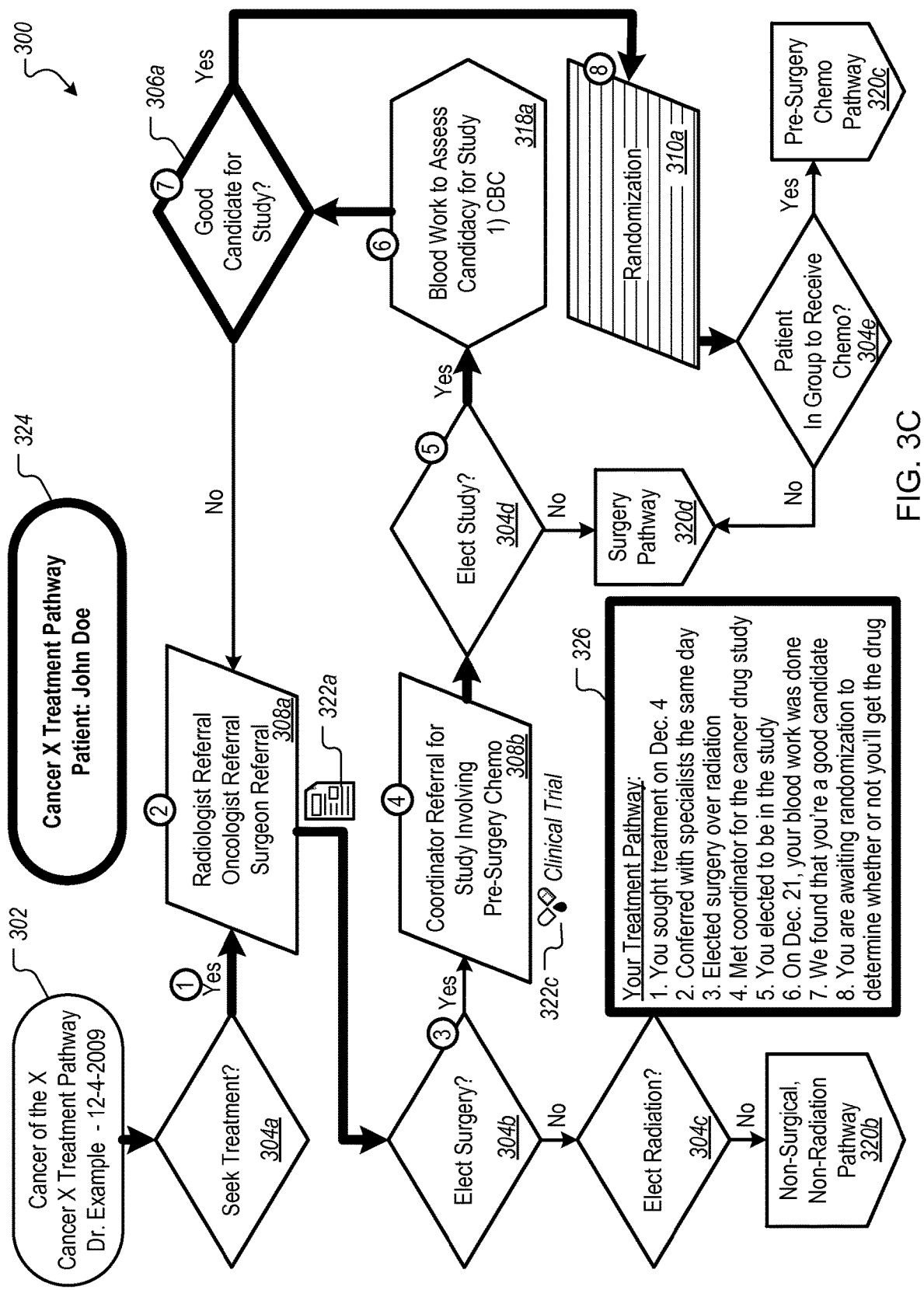
FIG. 3C shows an example of the pathway that is highlighted for the treatment of a particular patient.

FIG. 3C shows an example of the pathway 300 that is highlighted for the treatment of a particular patient. For example, a patient header 324 can identify the patient (e.g., John Doe) who is undergoing treatment, e.g., getting treated for cancer X following a path in the pathway 300. In this instantiation of the pathway 300, portions of the pathway 300 are highlighted to reflect a path associated with the treatment of the particular patient John Doe. In this example, the highlighting is done using thick lines on the arrows connecting elements in the pathway 300. Other designation techniques can be used, e.g., color-coding, shading, or other techniques to differentiate the patient's path from elements of the path not pertinent to the patient, or by graying out portions of the pathway that are not pertinent and/or no longer accessible by the patient. Similarly, different colors and/or other visual cues may be used to indicate patient-specific toxicities, responses and/or other outcomes.

The example in FIG. 3C is an augmented version of the pathway 300, as the markings and information described above with respect to FIGS. 3A-3B are present. In some implementations, a forward-looking version of the pathway 300 can be presented that indicates a current treatment point for the particular patient. For example, a clinical summary breadcrumb trail 326 lists decisions and selections made previously by the patient that resulted in the traversal of the path to the current point. The current point in this example is at the eighth step numbered in the clinical summary breadcrumb trail 326 and in the pathway 300, e.g., at the randomization work-up 310a, at which the patient is waiting to learn whether or not he will receive the an experimental cancer chemo-therapy drug prior to surgery.

In some implementations, the forward-looking version of the pathway can be presented in one frame of a user interface, and the clinical summary breadcrumb trail 326 can be presented in a second different frame of the user interface.

In some implementations, selecting one of the elements of the pathway 300 can cause additional elements to become highlighted. For example, while viewing the pathway 300, if the patient selects the "Yes" arrow, portions of the pathway 300 can be highlighted (e.g., in yet another color) to indicate elements in the path that may apply to the patient, e.g., if the patient is to receive the chemo drug.

Figure 3D:
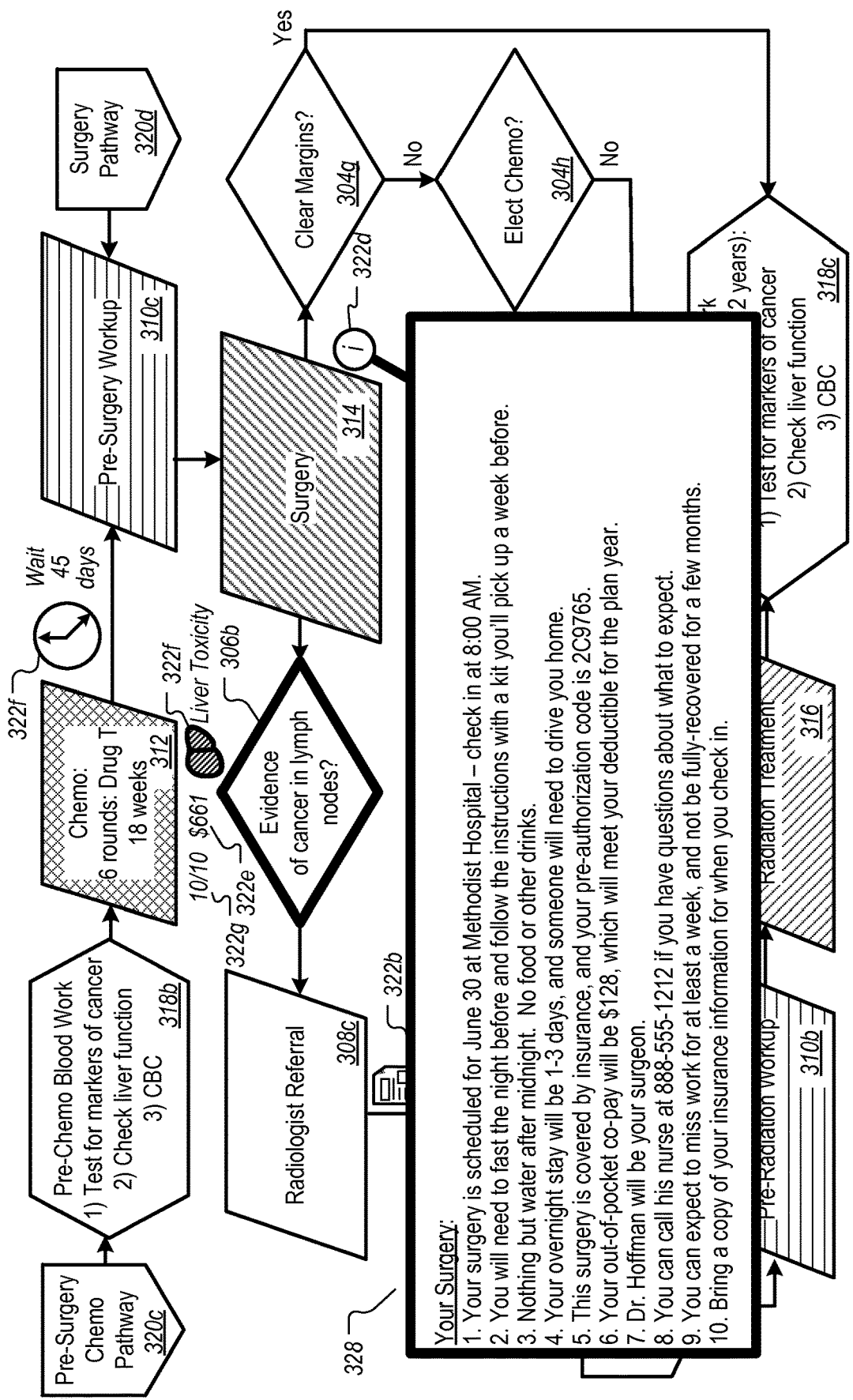
FIG. 3D shows example drill-down information accessible from a control on a pathway.

FIG. 3D shows example drill-down information accessible from a control on a pathway. For example, if the user selects the informational control 322d corresponding to and adjacent to the surgical treatment element 314, then drill-down information 328 can be displayed. The drill-down information can provide, for example, detailed information about the surgery that is represented by the surgical treatment element 314. The information can be very specific, e.g., if the surgery is planned for the next few days, or very general, e.g., if the surgery is not yet scheduled but the patient wants some general information.

Information in this example of drill-down information and other examples can be accessed automatically from various sources. In the current example, surgery dates and times that appear in drill-down information 328 can be pulled automatically from EMR of the patient and/or hospital scheduling information. Other types of drill-downs can provide ways for patients, physicians or other medical staff to enter information. For example, the drill-downs can include links that integrate with other systems.

Figure 3E:
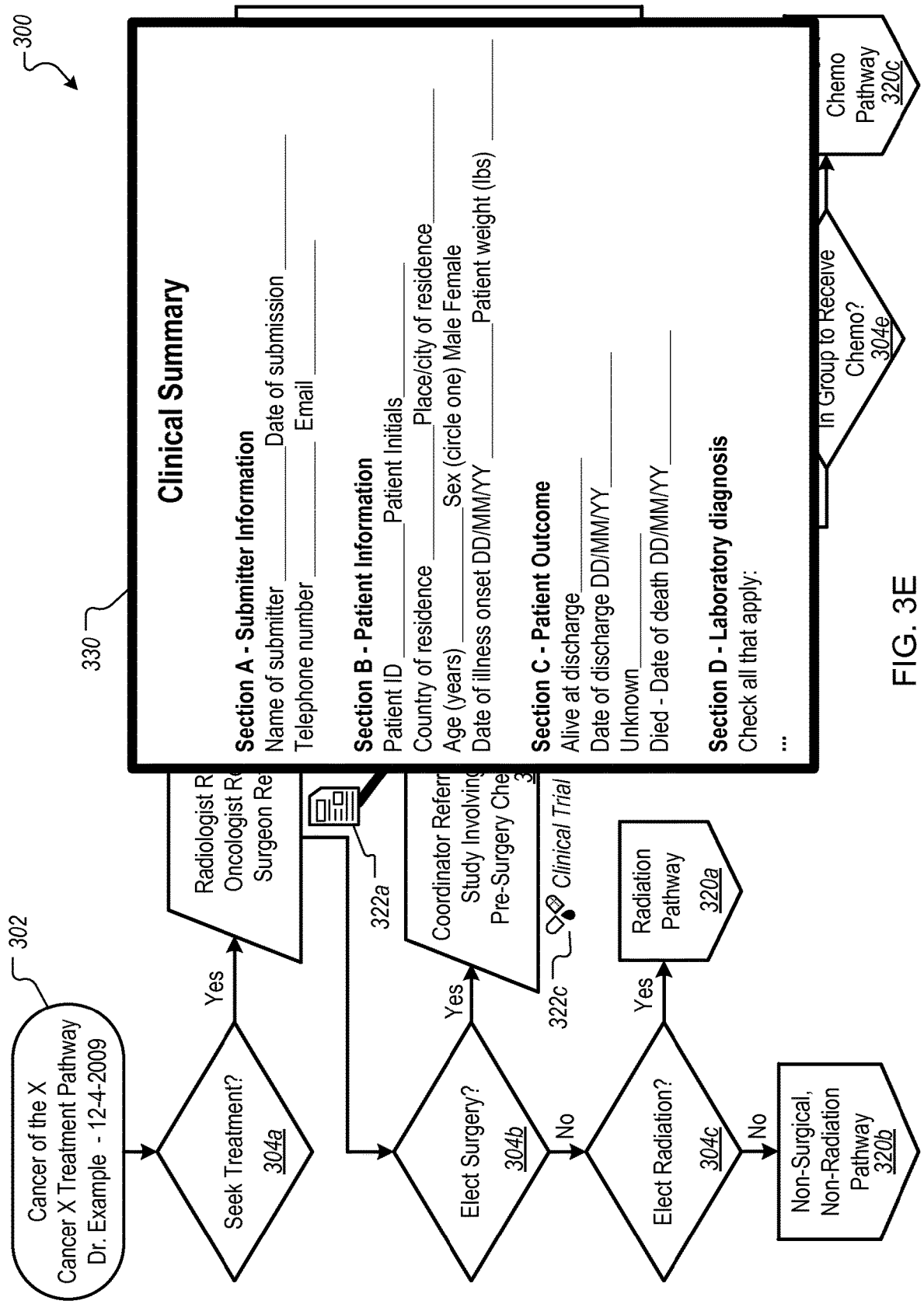
FIG. 3E is an example of drill-down information that is related to clinical summary information.

FIG. 3E is an example of drill-down information 330 that is related to clinical summary information. The drill-down information 330 may be presented, for example, upon user selection of the control 322a. For example, the information can be presented in a form that is integrated with other systems, including EMR systems. As such, current information in the form can be pulled automatically from various sources providing current data for presentation to the viewer. The drill-down information 330 and other types of drill-down information can include controls, e.g., for emailing, printing, saving, updating, synching, or other types of actions that may be performed in association with the information.

Figure 4:
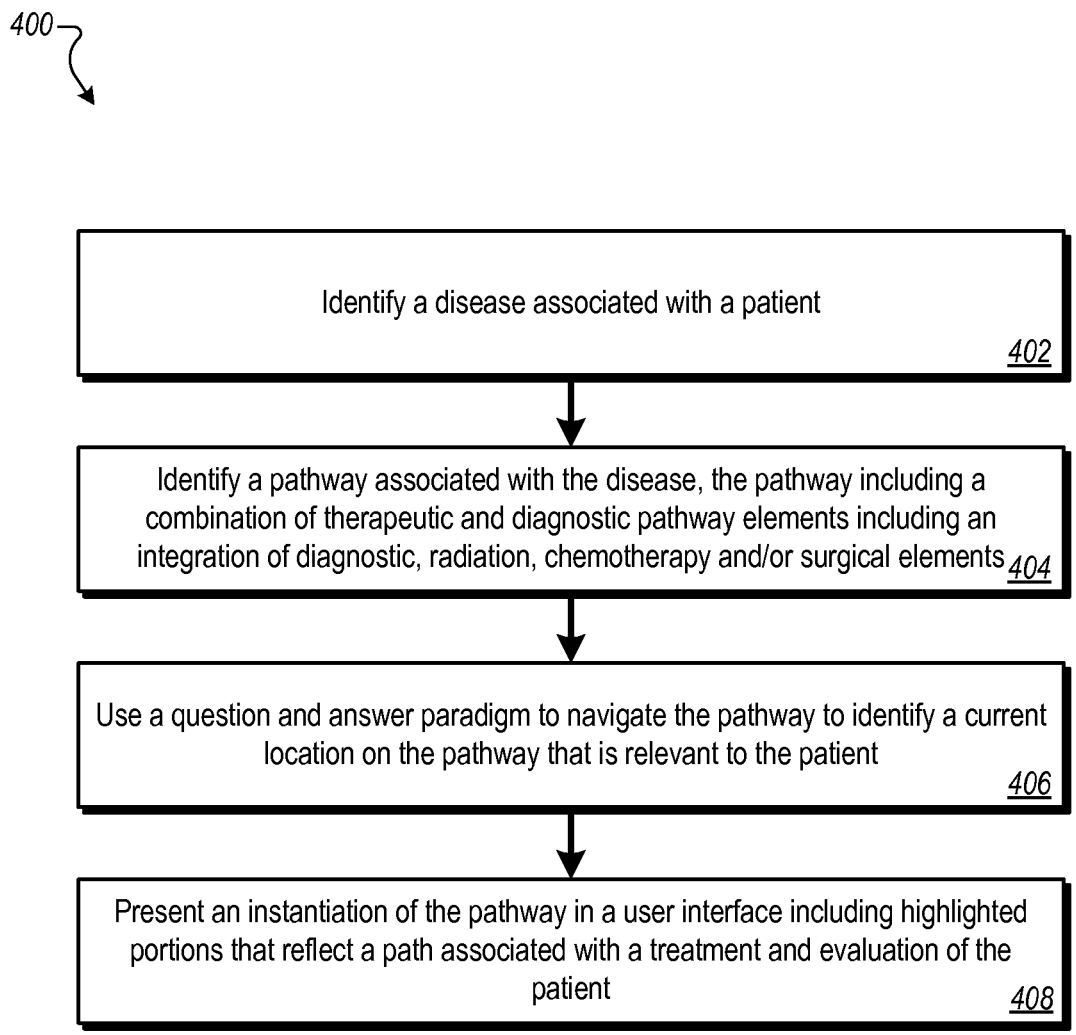
FIG. 4 is a flow diagram of an example process for presenting a patient-specific pathway.

FIG. 4 is a flow diagram of an example process 400 for presenting a patient-specific pathway. In some implementations, components of the treatment path server system 110 can perform steps of the process 400 using instructions that are executed by one or more processors. FIG. 1 is used to provide example structures for performing the steps of the process 400.

A disease associated with a patient is identified (402). As an example, using the computer device 108, a physician can identify a specific form of cancer associated with the physician's patent.

A pathway associated with the disease is identified that includes a combination of therapeutic and diagnostic pathway elements including an integration of diagnostic, radiation, chemotherapy and/or surgical elements (404). For example, the information retrieval engine 112 can access the pathways data 104 to find one or more pathways that correspond to the identified disease. The pathways can also indicate complications, prevention strategies, discharge planning, or other aspects of patient care and planning. The specific pathway(s) identified can further be based on other inputs provided by the physician, e.g. the age and gender of the patient, the progression of the disease and/or other factors.

Using a question and answer paradigm to navigate the pathway, a current location on the pathway is identified that is relevant to the patient (406). As an example, the physician can provide inputs in response to questions provided on the computer device 108. Example inputs include whether other treatments have already occurred, the wishes of the patient in fighting the disease, whether the patient is eligible for one or more clinical trials associated with the disease, and other factors. In some implementations, using the question and answer paradigm to navigate the pathway to identify the current location on the pathway that is relevant to the patient can further comprise linking the pathway to an EMR for the patient to facilitate navigation of the pathway. In some implementations, facilitating navigation of the pathway can further include providing answers to one or more questions based on information stored in the EMR during navigation.

An instantiation of the pathway is presented in a user interface, including highlighted portions that reflect a path associated with a treatment and evaluation of the patient (408). For example, using information that has been entered by the physician/patient or others and information extracted from the EMRs 106 associated with the patient, the augmentation engine 116 can produce a version of the pathway that is unique to the patient.

In some implementations, additional controls can exist. For example, a control can be provided for expanding or contracting the pathway, for providing a clinical summary, for expanding or contracting the clinical summary and other functions. In some implementations a control is included for enabling display of the pathway from a current time point forward, the current time point backward, the entire pathway, or some other time frame. For example, expanding or contracting the clinical summary for some other time frame can include providing an expanded portion of the pathway for a first portion of the time frame along with a contracted portion of the pathway for a second portion of the time frame.

In some implementations, the process 400 further includes collecting key therapy-related clinical outcomes information regarding both efficacy and toxicity. For example, the collected information can support assessment of the clinical pathways practice alignment as well as to support appropriate research data collection for biomarker discovery and/or clinical trial matching.

In some implementations, the process 400 further includes receiving data input associated with the pathway and providing at least one clinical summary that is color-coded and expandable based at least in part on responsibilities or needs of a viewing party. For example, the data input can include data received automatically from data capture tools integrated into an EMR and data received from manual inputs of medical staff or a patient.

Figure 5:
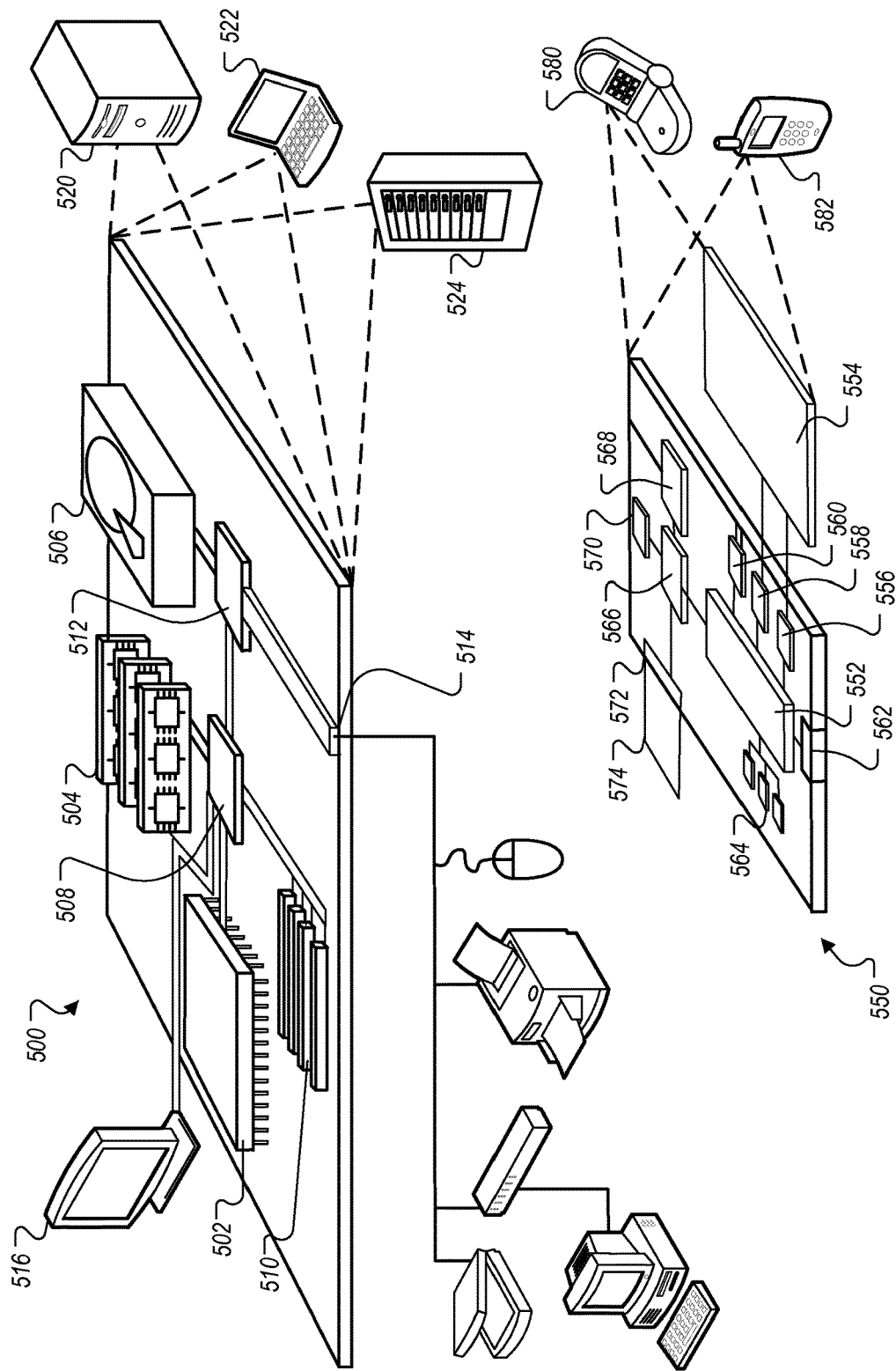
FIG. 5 is a block diagram of computing devices that may be used to implement the systems and methods described in this document Like reference numbers and designations in the various drawings indicate like elements.

FIG. 5 is a block diagram of computing devices 500, 550 that may be used to implement the systems and methods described in this document, as either a client or as a server or plurality of servers. Computing device 500 is intended to represent various forms of digital computers, such as laptops, desktops, workstations, personal digital assistants, servers, blade servers, mainframes, and other appropriate computers. Computing device 500 is further intended to represent any other typically non-mobile devices, such as televisions or other electronic devices with one or more processors embedded therein or attached thereto. Computing device 550 is intended to represent various forms of mobile devices, such as personal digital assistants, cellular telephones, smartphones, and other computing devices. The components shown here, their connections and relationships, and their functions, are meant to be exemplary only, and are not meant to limit implementations of the inventions described and/or claimed in this document.

Computing device 500 includes a processor 502, memory 504, a storage device 506, a high-speed interface 508 connecting to memory 504 and high-speed expansion ports 510, and a low speed interface 512 connecting to low speed bus 514 and storage device 506. Each of the components 502, 504, 506, 508, 510, and 512, are interconnected using various busses, and may be mounted on a common motherboard or in other manners as appropriate. The processor 502 can process instructions for execution within the computing device 500, including instructions stored in the memory 504 or on the storage device 506 to display graphical information for a GUI on an external input/output device, such as display 516 coupled to high speed interface 508. In other implementations, multiple processors and/or multiple buses may be used, as appropriate, along with multiple memories and types of memory. Also, multiple computing devices 500 may be connected, with each device providing portions of the necessary operations (e.g., as a server bank, a group of blade servers, or a multi-processor system).

The memory 504 stores information within the computing device 500. In one implementation, the memory 504 is a computer-readable medium. In one implementation, the memory 504 is a volatile memory unit or units. In another implementation, the memory 504 is a non-volatile memory unit or units. Some implementations can include various engines for controlling the generation of pathways and/or to access or provide information for use in pathways. For example, a metadata engine and/or other engines can be configured to drive questions, responses, drill-downs and logical flow of the question and answer interface.

The storage device 506 is capable of providing mass storage for the computing device 500. In one implementation, the storage device 506 is a computer-readable medium. In various different implementations, the storage device 506 may be a floppy disk device, a hard disk device, an optical disk device, or a tape device, a flash memory or other similar solid state memory device, or an array of devices, including devices in a storage area network or other configurations. In one implementation, a computer program product is tangibly embodied in an information carrier. The computer program product contains instructions that, when executed, perform one or more methods, such as those described above. The information carrier is a computer- or machine-readable medium, such as the memory 504, the storage device 506, or memory on processor 502.

The high speed controller 508 manages bandwidth-intensive operations for the computing device 500, while the low speed controller 512 manages lower bandwidth-intensive operations. Such allocation of duties is exemplary only. In one implementation, the high-speed controller 508 is coupled to memory 504, display 516 (e.g., through a graphics processor or accelerator), and to high-speed expansion ports 510, which may accept various expansion cards (not shown). In the implementation, low-speed controller 512 is coupled to storage device 506 and low-speed expansion port 514. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. It may also be implemented as part of a rack server system 524. In addition, it may be implemented in a personal computer such as a laptop computer 522. Alternatively, components from computing device 500 may be combined with other components in a mobile device (not shown), such as device 550. Each of such devices may contain one or more of computing device 500, 550, and an entire system may be made up of multiple computing devices 500, 550 communicating with each other.

Computing device 550 includes a processor 552, memory 564, an input/output device such as a display 554, a communication interface 566, and a transceiver 568, among other components. The device 550 may also be provided with a storage device, such as a microdrive or other device, to provide additional storage. Each of the components 550, 552, 564, 554, 566, and 568, are interconnected using various buses, and several of the components may be mounted on a common motherboard or in other manners as appropriate.

The processor 552 can process instructions for execution within the computing device 550, including instructions stored in the memory 564. The processor may also include separate analog and digital processors. The processor may provide, for example, for coordination of the other components of the device 550, such as control of user interfaces, applications run by device 550, and wireless communication by device 550.

Processor 552 may communicate with a user through control interface 558 and display interface 556 coupled to a display 554. The display 554 may be, for example, a TFT LCD display or an OLED display, or other appropriate display technology. The display interface 556 may comprise appropriate circuitry for driving the display 554 to present graphical and other information to a user. The control interface 558 may receive commands from a user and convert them for submission to the processor 552. In addition, an external interface 562 may be provided in communication with processor 552, so as to enable near area communication of device 550 with other devices. External interface 562 may provide, for example, for wired communication (e.g., via a docking procedure) or for wireless communication (e.g., via Bluetooth or other such technologies).

The memory 564 stores information within the computing device 550. In one implementation, the memory 564 is a computer-readable medium. In one implementation, the memory 564 is a volatile memory unit or units. In another implementation, the memory 564 is a non-volatile memory unit or units. Expansion memory 574 may also be provided and connected to device 550 through expansion interface 572, which may include, for example, a subscriber identification module (SIM) card interface. Such expansion memory 574 may provide extra storage space for device 550, or may also store applications or other information for device 550. Specifically, expansion memory 574 may include instructions to carry out or supplement the processes described above, and may include secure information also. Thus, for example, expansion memory 574 may be provide as a security module for device 550, and may be programmed with instructions that permit secure use of device 550. In addition, secure applications may be provided via the SIM cards, along with additional information, such as placing identifying information on the SIM card in a non-hackable manner.

The memory may include for example, flash memory and/or MRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 564, expansion memory 574, or memory on processor 552.

Device 550 may communicate wirelessly through communication interface 566, which may include digital signal processing circuitry where necessary. Communication interface 566 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 568. In addition, short-range communication may occur, such as using a Bluetooth, WiFi, or other such transceiver (not shown). In addition, GPS receiver module 570 may provide additional wireless data to device 550, which may be used as appropriate by applications running on device 550.

Device 550 may also communicate audibly using audio codec 560, which may receive spoken information from a user and convert it to usable digital information. Audio codec 560 may likewise generate audible sound for a user, such as through a speaker, e.g., in a handset of device 550. Such sound may include sound from voice telephone calls, may include recorded sound (e.g., voice messages, music files, etc.) and may also include sound generated by applications operating on device 550.

The computing device 550 may be implemented in a number of different forms, as shown in the figure. For example, it may be implemented as a cellular telephone 580. It may also be implemented as part of a smartphone 582, personal digital assistant, or other mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A computer-implemented method of generating a patient-specific augmented treatment pathway for treating a particular patient comprising:

receiving a request to display a pathway for a disease;
determining basic pathway data for the disease from a collection of pathways data;
presenting in a user interface the pathway, the pathway for use in treating the particular patient with a disease and including a combination of therapeutic and diagnostic pathway elements including an integration of diagnostic, radiation, chemotherapy, surgical elements and/or other elements including those related to other procedures, disciplines or pharmacotherapy;
in response to a request to present an augmented pathway, modifying the presented pathway presented from the basic pathway data according to a plurality of augmentations, the augmentations including retrieving information for the particular patient from one or more data sources and combining the retrieved data with information in the pathway data to perform augmentations comprising:
augmenting the pathway including generating one or more controls to add to the pathway, the one or more controls for accessing additional information associated with a given pathway element;
augmenting pathway elements to include indicators for pricing, efficacy and/or toxicity of a treatment associated with a given treatment element in the pathway;
augmenting the pathway with a connection to another pathway including providing a link to another pathway at a point in a given pathway to enable quick reference to the another pathway from a relevant point of the given pathway;
augmenting the pathway to incorporate patient-specific information for the particular patent;
presenting an augmented pathway in a user interface to the particular patient or treating physician, wherein the augmented pathway incorporates the modifications of the basic pathway data according to the plurality of augmentations; and
treating the particular patient with one or more of chemotherapy, surgery, or radiation according to the augmented pathway including using the augmented pathway to determine a prospective portion of the pathway representing a current decision point and future treatment decisions for treatment of the disease, wherein the future treatment decisions are determined based on the augmentations from the patient-specific information.

2. The method of claim 1 wherein the pathway is specific to a form of cancer.

3. The method of claim 1 wherein providing one or more controls further includes identifying one or more references germane to or for inclusion in a pathway, identifying updates or comments to the references, and providing one or both when the control is activated.

4. The method of claim 1 wherein the indicators for pricing include an estimate of one or more of a wholesale price, co-payments or actual cost, profit or other raw or evaluated financial indicators of a treatment associated with a pathway element and wherein the method further includes determining one or more of an estimate for a wholesale price, co-payments, an actual cost, profit or other raw or evaluated financial indicators for the treatment.

5. The method of claim 1 wherein the indicators include indicators of effectiveness of treatment or indicators of appropriateness of a treatment.

6. The method of claim 1 wherein the indicators for toxicity and/or efficacy include a toxicity and/or efficacy score, and wherein the method further includes calculating a toxicity and/or efficacy score based at least in part on historical information associated with treatment of patients using the pathway.

7. The method of claim 1 wherein the pathway includes plural integrated pathways.

8. The method of claim 1 further comprising color-coding the elements based on a type of element such that different therapeutic or diagnostic element types are color-coded to reflect the type of element.

9. The method of claim 1 wherein the color coding includes color coding individual pathway elements and color coding blocks of elements to define particular portions of the pathway.

10. The method of claim 1 wherein the additional information includes information to assist in making a decision in association with a decision element in the pathway, clarification information for an element, patient education information, or decision rationale information.

11. The method of claim 1 further comprising augmenting one or more pathway elements with referral information when the pathway element involves a treatment that is beyond a scope of a current treatment facility.

12. The method of claim 11 wherein augmenting the one or more pathway elements with referral information further includes augmenting a pathway element with a control for directly referring a patient to another treating facility or care provider.

13. The method of claim 1 further comprising linking the pathway to an electronic medical record for the patient.

14. A method for generating and presenting treatment information comprising a patient-specific augmented treatment pathway to treat a particular patient to the particular patient or treatment professional comprising:
identifying a disease associated with a patient;
identifying a pathway associated with the disease, the pathway including basic pathway data for the disease including a combination of therapeutic and diagnostic pathway elements including an integration of diagnostic, radiation, chemotherapy and/or surgical elements;
using a question and answer paradigm to navigate the pathway to identify a current location on the pathway that is relevant to the particular patient;
modifying the pathway based on the question and answer paradigm and patient specific data of the particular patent to generate an augmented pathway specific to the particular patient including retrieving information for the particular patient from one or more data sources and combining the retrieved data with information in the pathway;
presenting an instantiation of the augmented pathway in a user interface including highlighted portions that reflect a path associated with a treatment and evaluation of the particular patient; and
treating the particular patient with one or more of chemotherapy, surgery, or radiation according to the augmented pathway including using the augmented pathway to determine a prospective portion of the pathway representing a current decision point and future treatment decisions for treatment of the disease, wherein the future treatment decisions are determined based on the augmentations from the patient-specific information.

15. The method of claim 14 wherein presenting the instantiation of the pathway further includes presenting a forward-looking version of the pathway from a current treatment point for the particular patient and presenting a breadcrumb trail or clinical summary in an outline format and/or graphical format for decisions and selections made previously that resulted in a traversal of the path to the current point.

16. The method of claim 15 wherein the forward looking version of the pathway is presented in one frame of a user interface and the clinical summary or breadcrumb trail is presented in a second different frame of the user interface.

17. The method of claim 15 further comprising receiving a selection of an element in the forward looking version breadcrumb trail and the method further comprising presenting an instantiation of the pathway from a point in the pathway associated with the selection including a highlighted portion reflecting the path traversed in treating the patient.

18. The method of claim 14 wherein the pathway is an augmented pathway that includes one or more controls for accessing additional information associated with a given pathway element to assist in either evaluating a pathway element or making a decision in association with a decision element in the pathway and one or more indicators for pricing, efficacy and/or toxicity or outcomes of a treatment associated with a given treatment element in the pathway.

19. The method of claim 14 wherein the pathway provides a clinical summary of past treatment of and potential future treatment options for the patient.

20. The method of claim 19 further comprising providing a control for expanding or contracting the clinical summary including a control for enabling display of the pathway from a current time point forward, the current time point backward, the entire pathway, or some other time frame.

21. The method of claim 19 wherein the some other time frame includes providing an expanded portion of the pathway for a first portion of the time frame along with a contracted portion of the pathway for a second portion of the time frame.

22. The method of claim 14 wherein using the question and answer paradigm to navigate the pathway to identify the current location on the pathway that is relevant to the patient further comprises linking the pathway to an electronic medical record for the patient to facilitate navigation of the pathway.

23. The method of claim 22 wherein facilitating further includes providing answers to one or more questions based on information stored in the electronic medical record during navigation.

24. The method of claim 1 wherein the additional information includes periodicals, drill-down information, teaching tools, resources or presentations.

25. The method of claim 14 further including:
receiving data input associated with the pathway, the data input including data received automatically from data capture tools integrated into an electronic medical record and data received from manual inputs of medical staff or a patient; and
providing at least one clinical summary that is color-coded and expandable based at least in part on responsibilities or needs of a viewing party.

26. The method of claim 1 wherein the another pathway is selected from the group comprising nursing, discharge, planning, complications or prevention pathways.

27. The method of claim 1, wherein augmenting the pathway to incorporate patient-specific information includes using patient data to determine a location of the patient on the pathway and visually indicating portions of the path that are no longer available to the patient.

28. The method of claim 1, wherein augmenting the pathway to incorporate patient-specific information includes using patient data to visually indicate portions of the pathway corresponding to a particular path being followed by the patient.

29. The method of claim 1, wherein in response to a user interaction with an element of the presented augmented pathway, visual indicators are presented indicating particular path elements that apply to the patient based on the user interaction.

* * * * *

UNITED STATES PATENT AND TRADEMARK OFFICE
CERTIFICATE OF CORRECTION

| | | |
|---|---|---|
| PATENT NO. | : 11,361,867 B2 | |
| APPLICATION NO. | : 14/433364 | |
| DATED | : June 14, 2022 | |
| INVENTOR(S) | : Alan F. List and Mark Gerard Schippits | |

It is certified that error appears in the above-identified patent and that said Letters Patent is hereby corrected as shown below:

On the Title Page

Item [71], delete "Insitute," and insert --Institute,--, therefor.

Signed and Sealed this
Second Day of August, 2022

Katherine Kelly Vidal
*Director of the United States Patent and Trademark Office*